United States Patent [19]

Vangermain et al.

[11] 4,305,844

[45] Dec. 15, 1981

[54] PROCESS FOR THE PREPARATION OF SILVER CATALYSTS FOR THE PRODUCTION OF ETHYLENE OXIDE

[75] Inventors: Erwin Vangermain; Willi Brauckmann; Hans-Jürgen Erberich; Horst Ueberschaer, all of Marl, Fed. Rep. of Germany

[73] Assignee: Chemische Werke Hüls AG, Marl, Fed. Rep. of Germany

[21] Appl. No.: 135,927

[22] Filed: Mar. 31, 1980

[30] Foreign Application Priority Data

Apr. 11, 1979 [DE] Fed. Rep. of Germany ....... 2914640

[51] Int. Cl.³ ..................... B01J 23/02; B01J 23/04; B01J 23/50
[52] U.S. Cl. .................. 252/443; 252/455 R; 252/463; 252/475; 252/476
[58] Field of Search ............... 252/463, 475, 476, 443, 252/455 R

[56] References Cited

U.S. PATENT DOCUMENTS

3,793,231  2/1974  Bergmann et al. ............. 252/476 X
4,066,575  1/1978  Winnick ............................. 252/475

*Primary Examiner*—W. J. Shine
*Attorney, Agent, or Firm*—Wells & Wells

[57] ABSTRACT

A process for preparing silver catalysts containing alkaline earth metals and alkali metals as promoters for the production of ethylene oxide by oxidizing ethylene with oxygen or oxygen-containing gases. The silver catalysts are prepared by:

(a) depositing a suspension consisting of silver oxide and an aqueous solution of an organic silver salt on a porous substrate, the molar ratio of the silver in the silver oxide to the silver in the silver salt being from about 35 to 65%, and periodically increasing the pressure (decreasing the vacuum) being used during the absorption;

(b) carrying out an interim drying as a thin moving bed in an inert gas atmosphere at temperatures between about 50° and 150° C. to prepare an interim product;

(c) depositing a further layer of the silver-containing suspension on the interim product in the manner described in step (a), this suspension additionally containing compounds of barium and cesium, rubidium or a mixture of cesium and rubidium in sufficient amounts that the finished catalyst contains from about 0.01 to 0.25% by weight of barium and from about 0.001 to 0.05% by weight of cesium, rubidium, or a mixture of cesium and rubidium, calculated as metals; and (d) heating to temperatures from about 160° to 270° C. as a thin moving bed.

6 Claims, No Drawings

PROCESS FOR THE PREPARATION OF SILVER CATALYSTS FOR THE PRODUCTION OF ETHYLENE OXIDE

CROSS REFERENCE TO RELATED APPLICATIONS

Applicants claim priority under 35 USC 119 for application P No. 29 14 640.5, filed Apr. 11, 1979 in the Patent Office of the Federal Republic of Germany.

The application of Erwin Vangermain et al entitled, "Process for Activating or Reactivating Ethylene Oxide Silver Substrate Catalysts", filed Mar. 31, 1980 and having Ser. No. 136,045 is incorporated herein to show an ethylene oxide process and apparatus wherein the present catalysts are useful.

BACKGROUND OF THE INVENTION

The field of the invention is improved silver catalysts for the production of ethylene oxide, their preparation and their use in ethylene oxide processes.

The state of the art of processes for preparing ethylene oxide by the catalytic vapor phase oxidation of ethylene with molecular oxygen in the presence of supported silver catalysts may be ascertained by reference to U.S. Pat. Nos. 4,012,425; 4,039,561; 4,051,068; and 4,125,480, the disclosures of which are incorporated herein. U.S. Pat. Nos. 3,793,231; 3,962,136; 4,066,575 and 3,875,080 disclose the state of the art of silver catalysts for the production of ethylene oxide, the disclosures of which are incorporated herein.

The production of ethylene oxide by the oxidation of ethylene is carried out in the presence of catalysts containing silver. The catalysts used for the oxidation of ethylene into ethylene oxide essentially are prepared by:

(a) depositing an active silver layer by means of a suspension onto a substrate (suspension method) where mechanical mixing or spraying techniques are employed; or (b) impregnating a porous substrate material with a silver salt solution (impregnation method); the catalysts then being subjected to post-thermal treatment.

With regard to the so-called "suspension method", usually an aqueous suspension of silver oxide is placed on a ceramic substrate material. A cohesive silver layer of varying thickness, depending in the case, is formed on the substrate and then activated. This layer of silver is quite susceptible to damage, whereby silver dust accumulates throughout the reactor tube and causes an increased pressure difference. This pressure difference leads to a decrease in the gas flow and hence to a drop in reactor output. To avoid this drawback, every effort is made so that the silver oxide particles penetrate as deeply as possible into the substrate pores in order to protect them against mechanical abrasion and thus to increase catalyst life.

According to the so-called "impregnation process", an aqueous solution of a silver salt is used in lieu of a suspension of a silver oxide, and the substrate is dipped into this aqueous solution. After absorption of the silver compound into the substrate pores, the impregnated substrate is dried and post-treated thermally. These catalysts suffer from the pronounced drawback that they allow only a low conversion even though they evince good selectivity.

It is furthermore known to add modifying agents (promoters) to the catalysts. Predominantly the compounds of the alkaline earth metals, alkali metals and rare earth metals are recommended as these promoters. Furthermore the addition of alkali metals, especially the "heavy" alkali metals, potassium, rubidium and cesium are known as disclosed in U.S. Pat. Nos. 3,962,136 and 4,066,575. The reports about the optimal preparation of such catalysts are conflicting. These conflicting results are disclosed with respect to selectivity and extent of conversion at a given temperature of reaction depending on whether the promoter is worked into the substrate during a prior process step, during the deposition of the silver compound or after the preparation of the primary silver catalyst.

An especially advantageous process for preparing silver catalysts for the production of ethylene oxide is disclosed in U.S. Pat. No. 3,793,231, and this process is termed herein as a "mixed process". According to the "mixed process" use is made of an aqueous silver oxide suspension wherein a given part of the silver is present as a silver salt. This process achieves both the advantages of the above mentioned impregnation method and those of the suspension method, without incurring the drawbacks of either.

SUMMARY OF THE INVENTION

Having in mind the limitations of the suspension and impregnation methods of preparing silver catalysts for use in the catalytic vapor phase oxidation of ethylene with molecular oxygen, it is an object of the present invention to improve upon the mixed process for preparing the silver catalysts.

According to the present invention, silver catalysts containing alkaline earth metals and alkali metals as promoters for the production of ethylene oxide by oxidizing ethylene with oxygen or oxygen-containing gases are prepared by:

(a) depositing a suspension consisting of silver oxide and an aqueous solution of an organic silver salt on a porous substrate, the molar ratio of the silver in the silver oxide to the silver in the silver salt being from 35 to 65%, with the use of periodically decreased pressure during the absorption;

(b) drying of the deposited silver compounds as a thin moving bed in an inert gas atmosphere at temperature between about 50° and 150° C. to form an interim product;

(c) deposition of a further layer of the silver-containing suspension on the interim product as in (a), this further suspension additionally containing compounds of barium and cesium, rubidium or a mixture thereof in sufficient amounts that the finished catalyst contains from about 0.01 to 0.25% by weight of barium and from about 0.001 to 0.05% by weight of cesium, ribidium or a mixture of cesium and rubidium, calculated as metals; and (d) heating the deposited silver compounds to temperatures from about 160° to 270° C. as a thin moving bed.

The catalysts obtained are especially active and permit not only high selectivity but also a high space time yield.

DESCRIPTION OF THE PREFERRED EMBODIMENTS

The catalysts of the present invention appropriately are prepared as follows:

First silver oxide is precipitated from an aqueous solution of a silver salt, typically silver nitrate, with an aqueous solution of sodium or potassium hydroxide. The silver oxide is then filtered off and washed with distilled water until the rinse drains salt free. From 35 to 65 mole %, advantageously from 45 to 55 mole %, especially 50 mole % of the silver oxide are converted into soluble silver salt using an organic acid.

The mixture so obtained is placed together with the refractory substrate into a rotatable mixing vessel having a heater. At temperatures between about 20° and 100° C., the aqueous mixture of silver oxide and silver salt is deposited at reduced pressure on and into the substrate pores. The vacuum applied is varied periodically in that, by short-term ventilation, the pressure is permitted to increase (with decreasing vacuum)—though not to full atmospheric pressure. The frequency of pressure changes depends on the ambient conditions, i.e. the pore diameter of the substrate. As a rule, each change in pressure (decrease in vacuum) is implemented once per minute. Typically, the vacuum is periodically reduced 25 to 55 mbars per each minute.

Monobasic, dibasic or tribasic organic acids are used for the partial conversion of the silver oxide first formed, by converting them into a water-soluble silver salt. The anion in the silver salt is not critical, though it should be one which will not form catalyst poisons. Suitable substances are organic carboxylic acids such as formic acid, acetic acid, oxalic acid, malonic acid, glutaric acid. Such hydroxycarboxylic acids as lactic acid, citric acid, tartaric acid or glycolic acid are also suitable. Advantageously silver lactate is used as the silver salt and lactic acid as the corresponding organic carboxylic acid.

The moist catalyst is subjected to an interim drying step. It is essential that the drying be carried out in a thin moving bed in an inert atmosphere, the inert gas being moved in counterflow. Nitrogen is advantageous as the inert gas. The temperature used is in the range from about 50° to 150° C., advantageously at 120° C., especially at 110° C. The temperature difference within the belt can be up to 10° C. A thin bed means a bed height that will not substantially exceed twice the catalyst grain diameter. Wire cloth machines equipped with V4A wire cloth were found particularly advantageous, where heating of the wire cloth belt of conveyor is possible from above and below. As a rule the dwell time is from about 10 to 720 minutes, in particular from about 30 to 300 minutes. The dwell time can be controlled by the linear speed of the wire cloth.

In the next step, a further layer of silver is deposited on the substrate, again an aqueous suspension of silver oxide and silver salt is deposited under the conditions stated above. In this process stage however, compounds of barium and rubidium or cesium or a mixture of rubidium and cesium are added to the suspension. The compounds of these promoter metals preferably are water soluble. Particularly suitable substances are barium peroxide, rubidium nitrate, cesium nitrate, or the hydroxides, especially the lactic acid salts of barium, rubidium and cesium. Obviously the compounds should not contain ingredients known as catalyst poisons such as sulfur compounds, iron oxides and amalgams and chlorine compounds.

The proportions of the compounds added are measured in the finished catalyst, and calculated as metals. The concentrations are from about 0.01 to 0.25% by weight, preferably 0.02%, in particular 0.05% by weight of barium and from about 0.001 to 0.05% by weight, preferably 0.007 to 0.015% by weight, in particular 0.01% by weight of rubidium, cesium or a mixture of rubidium and cesium.

Thereupon the treated catalyst is again dried in the form of a thin bed or it is directly activated when in the form of a thin moving bed. Appropriately this is carried out in another wire cloth machine which is similarly equipped with steaming registers. Activation takes place at about 160° to 270° C., preferably at 250° C., especially at 240° C. Advantageously there is from 0 to 8% by volume of oxygen present during the activation. Reducing gases such as hydrogen or ethane also may be present.

The difference in temperature across the belt can be controlled well and as a rule, it should not exceed 10° C., in particular not more than 50° C.

The catalysts so obtained evince a very low glow-heat loss of less than 1.5% by weight, in particular less than 0.5% by weight.

The silver content of the catalyst is from about 5 to 25% by weight, especially from 9 to 21% by weight. The refractory substrate used for the preparation of the catalysts can be in the form of spheres, rings, pellets or such bodies causing minimal pressure drop in the reaction tube. Those refractory substrates are preferred which consist predominantly of alpha aluminum oxide. Other examples of the substrates include alpha aluminum oxide containing up to 20 percent by weight silicon dioxide, or silicon carbide.

The apparent porosity is between 35 and 65%, especially between 40 and 60%, advantageously 55%. The pore diameter for instance is between 1 and 100 microns for 35 to 90% of the material and 60% of it is between 100 and 500 microns.

The specific surface advantageously is less than 10 $m^2/g$, especially less than 1 $m^2/g$. The diameter of the individual substrates advantageously is in the range from 5 to 10 mm.

Typical conditions of oxidation are selected when using the catalysts of the present invention: temperatures of reaction between about 200° and 300° C. and pressures of reaction between about 5 and 30 bars. The input gas mixture of the starting material comprises 0.5 to 40% by volume of ethylene, 0 to 60% by volume of methane, 1 to 15% by volume of oxygen and the remainder comprises other inert ingredients such as nitrogen, carbon dioxide or argon. In industrial practice, this mixture of gases is moved over the catalyst in circulating manner, the ethylene oxide being formed is separated, the carbon dioxide is removed in part, and after addition of more starting materials, the gas mixture is again passed over the catalyst.

The preparation of the silver catalysts of the present invention and the application of these catalysts in the production of ethylene oxide are described in detail below in the following examples.

EXAMPLE 1

(1) Preparing the Catalyst 8,000 g of silver nitrate (47 moles) are dissolved in 200 liters of fully desalted water. A solution of 1,950 g of sodium hydroxide in 6 liters of fully desalted water are added slowly with stirring at room temperature for the purpose of precipitating the silver oxide, whereby the temperature does not exceed 25° C. The precipitated silver oxide is suction-filtered and slowly washed with fully desalted water until the draining rinse is salt free. 50% of the silver oxide precipitate is converted into silver lactate by adding the stoichiometric amount of lactic acid. The remainder of the silver oxide is added to the aqueous silver lactate solution.

Thereupon this mixture is combined with 40 kg of a porous support material consisting of a mixture of 86% for weight aluminum oxide and 12% by weight silicon dioxide in a Dragier drum which is adapted to heating and evacuation. At a temperature between 85° and 95° C. and a pressure of about 105 mbars and an angular speed of about 10 rpm in the Dragier drum, the mixture of silver oxide and silver lactate is deposited into and onto the substrate. The pressure is elevated approximately once per minute by short-term ventilation to 130–160 mbars. After about 30 minutes, 85% of the water has been evaporated.

The catalyst thus produced is predried in sufficient amount under nitrogen flow at 125° C. on a wire cloth machine. The wire cloth belt consists of an interwoven V4A wire, with a width of 1.10 m and a length of 4.25 m×2; the belt speed is 6.77 cm/minute. This results in a dwell time of about 90 minutes for a catalyst bed thickness which is about twice the grain diameter. The belt is heated from above and below by steam registers.

Using a repetition of the above method, a further layer of active silver is introduced into the catalyst in the same manner. A solution of 6.7 g of cesium nitrate in water is added to the mixture of silver oxide and silver lactate and thereupon 30 g of barium peroxide are put into the Dragier drum.

(2) Activation

The catalyst thus predried is activated in a second wire cloth machine of analogous construction. The belt speed is 5.64 cm/min; therefore the dwell time is 75 min. The belt again is heated from steam registers from above and below. The highest temperature was 210° C., the temperature difference across the width of the belt was 5° C. Nitrogen with an oxygen content of 5% by volume was made to pass at a rate of 10 m$^3$/h in counterflow over the belt. Analysis of the finished catalyst shows it contains 19.45% by weight of silver, 481 ppm of barium and 91 ppm of cesium. A loss due to glowing of 0.4% by weight was ascertained in the catalyst thus produced, which loss mainly was water. The silver on the catalyst substrate adheres so firmly that the catalyst is dust-free when being refilled or shaken.

(3) Catalyst Testing

The catalyst is tested in an apparatus consisting of 6,000 mm long reaction tube with a 26 mm diameter, and made of stainless steel. The reaction tube is surrounded by a jacket containing water or water vapor for removing the heat of reaction.

The reaction tubing is filled with 2.7 liters=2.8 kg of the finally formed catalyst.

A gas mixture consisting of
25% by volume of $C_2H_4$
49% by volume of $CH_4$
6.8% by volume of $O_2$
4.5% by volume of $CO_2$
0.2% by volume of $C_2H_6$
remainder by volume of $Ar+N_2$ is made to pass at a rate of 20 m$^3$/h (stp) over the catalyst. The pressure in the reactor is 19.8 bars gauge and the temperature in the vapor chamber of the cooling jacket is 247° C. The total chlorine content of the input gas is 8 mg of Cl/m$^3$ (stp), being achieved by the special dosing of a moderator.

Upon completion of the start-up phase of the freshly filled catalyst, an oxygen conversion of 41 mole %, a selectivity of 79.1 mole % and an ethylene oxide concentration at the reactor discharge of 2.13 mole % were ascertained.

EXAMPLES 2a–2c

A series of catalysts with varying barium contents but constant cesium contents are prepared using the substrate of example 1 and the method described therein, and are tested in a manner analogous to example 1. The compositions and properties of the catalysts are listed in table 1.

EXAMPLES 3a–3c

Using the method described in example 1, a series of catalysts with varying cesium contents but constant barium content are prepared. The finished catalysts are investigated in similar manner. The results are listed in table 2.

EXAMPLES 4a–4b

As described in example 1, using the same substrate but cesium or rubidium metal additives, namely cesium nitrate or rubidium nitrate a series of catalysts was prepared and tested analogously to example 1. The results of this testing are listed in table 3.

EXAMPLES 5a–5b

Using the same method as described in example 1, a series of catalysts was prepared, using as different substrate materials, namely α-aluminum oxide, the addition of barium peroxide and cesium nitrate as promoters was retained.

These catalysts were tested as described in example 1; the test results are listed in table 4.

EXAMPLES 6a–6b

A series of catalysts with constant barium contents as in examples 3a–3c, but with rubidium and a mixture of rubidium and cesium are used in place of cesium. The results are listed in table 5.

TABLE 1

| Example | % Ag-content | barium ppm | cesium ppm | activation | steam-chamber temp. °C. | $O_2$ conversion mole % | ethylene oxide mole % | selectivity mole % |
|---|---|---|---|---|---|---|---|---|
| 2a | 19.8 | 97 | 85 | wire cloth | 254 | 37.2 | 1.97 | 79.3 |
| 2b | 19.7 | 223 | 89 | wire cloth | 251 | 40.2 | 2.07 | 78.5 |
| 2c | 19.5 | 470 | 81 | wire cloth | 248 | 40.3 | 2.11 | 79.0 |

TABLE 2

| Example | % Ag-content | barium ppm | cesium ppm | activation | steam-chamber temp. °C. | O₂ conversion mole % | ethylene oxide mole % | selectivity mole % |
| --- | --- | --- | --- | --- | --- | --- | --- | --- |
| 3a | 20.2 | 465 | 91 | wire cloth | 248 | 38.9 | 2.03 | 78.9 |
| 3b | 19.6 | 477 | 47 | wire cloth | 245 | 37.9 | 2.00 | 79.2 |
| 3c | 19.7 | 480 | 173 | wire cloth | 253 | 42.4 | 2.15 | 78.1 |

TABLE 3

| Example | % Ag-content | barium ppm | alkali ppm | activation | steam-chamber temp. °C. | O₂ conversion mole % | ethylene oxide mole % | selectivity mole % |
| --- | --- | --- | --- | --- | --- | --- | --- | --- |
| 4a | 19.5 | 471 | 90 (Cs) | wire cloth | 248 | 40.3 | 2.11 | 79.0 |
| 4b | 19.4 | 465 | 95 (Rb) | wire cloth | 253 | 41.2 | 2.03 | 77.3 |

TABLE 4

| Example | % Ag-content | barium ppm | cesium ppm | activation | steam-chamber temp. °C. | O₂ conversion mole % | ethylene oxide mole % | selectivity mole % |
| --- | --- | --- | --- | --- | --- | --- | --- | --- |
| 5a | 19.5 | 471 | 95 | wire cloth | 248 | 40.3 | 2.11 | 79.0 |
| 5b | 18.8 | 451 | 91 | wire cloth | 249 | 40.1 | 2.05 | 78.3 |

TABLE 5

| Example | % Ag-content | barium ppm | rubidium ppm | activation | steam-chamber temp. °C. | O₂ conversion mole % | ethylene oxide mole % | selectivity mole % |
| --- | --- | --- | --- | --- | --- | --- | --- | --- |
| 6a | 20.2 | 465 | 91 | wire cloth | 253 | 40.9 | 2.03 | 77.5 |
| 6b | 19.7 | 480 | 44 (cesium ppm 53) | wire cloth | 250 | 40.2 | 2.04 | 78.1 |

COMPARISON EXAMPLE

A catalyst prepared by the impregnation method and impregnated with 270 ppm of barium and 53 ppm of cesium by means of the silver salt solution after the activation, and which was not dried and activated in the form of a thin moving bed, was tested at a silver content of 14.1% by weight under the conditions described in example 1, (3), Catalyst Testing.

Upon completion of the start-up phase of the freshly filled catalyst, an oxygen conversion of 44.1% mole %, an ethylene oxide concentration of 1.91 mole % at the reactor discharge and a selectivity of 73.7 mole % were found at a steam chamber temperature of 258° C. and a total chlorine content of 6.3 mg of Cl/m³ (stp).

We claim:

1. In a process for the preparation of a supported silver catalyst containing alkaline earth metals and alkali metals as promoters suitable for the production of ethylene oxide by the oxidation of ethylene with gaseous oxygen or oxygen containing gases, the improvement comprising said catalyst preparation process comprising the following steps:
   (a) depositing in an evacuated container a suspension of silver oxide and an aqueous solution of an organic silver salt on a porous refractory substrate, the molar ratio of the silver in the silver oxide to the silver in the silver salt being from about 35 to 65% while periodically decreasing the vacuum;
   (b) drying the deposited silver compounds and porous refractory of (a) in a thin moving bed in an inert gas atmosphere at temperatures between about 50° and 150° C. to form an interim product;
   (c) depositing in said evacuated container a second suspension of silver oxide and a second aqueous solution of an organic silver salt on said interim product, the molar ratio of the silver in the silver oxide to the silver in the silver salt being from about 35 to 65%, said second suspension and said second aqueous solution suspension additionally containing compounds of barium and cesium or rubidium or a mixture of cesium and rubidium in sufficient amounts that the finished catalyst contains from about 0.01 to 0.25% by weight of barium and from about 0.001 to 0.05% by weight of cesium or rubidium or a mixture of cesium and rubidium, calculated as metals; and
   (d) activating the twice deposited silver compounds at temperatures of about 160° C. to 270° C. in a thin moving bed and in the presence of not more than about 8% oxygen.

2. The process of claim 1, wherein said drying step (b) is carried out a second time after step (c).

3. The process of claim 1, wherein the temperature difference across said thin moving bed is not more than about 10° C.

4. The process of claim 1, wherein said thin moving bed has a thickness not more than about twice the diameter of the catalyst grain.

5. The process of claim 1, wherein said periodically decreasing the vacuum is carried out once per minute with a 25 to 55 mbars reduction in vacuum.

6. The process of claim 1, wherein said porous refractory substrate is selected from the group consisting of alpha-aluminum oxide, alpha-aluminum oxide containing up to 20 percent by weight silicon dioxide and alpha-aluminum oxide containing up to 20 percent by weight silicon carbide.

* * * * *